(12) United States Patent
Koseoglu et al.

(10) Patent No.: US 9,285,307 B2
(45) Date of Patent: Mar. 15, 2016

(54) CHARACTERIZATION OF CRUDE OIL BY ULTRAVIOLET VISIBLE SPECTROSCOPY

(75) Inventors: Omer Refa Koseoglu, Dhahran (SA); Adnan Al-Hajji, Dammam (SA); Gordon Jamieson, London (GB)

(73) Assignee: Saudi Arabian Oil Company, Dhahran (SA)

( * ) Notice: Subject to any disclaimer, the term of this patent is extended or adjusted under 35 U.S.C. 154(b) by 631 days.

(21) Appl. No.: 13/400,865

(22) Filed: Feb. 21, 2012

(65) Prior Publication Data

US 2016/0011102 A1    Jan. 14, 2016

Related U.S. Application Data

(60) Provisional application No. 61/445,208, filed on Feb. 22, 2011.

(51) Int. Cl.
*G06F 19/00* (2011.01)
*G01N 21/33* (2006.01)
*G01N 33/28* (2006.01)

(52) U.S. Cl.
CPC ............ *G01N 21/33* (2013.01); *G01N 33/2811* (2013.01); *G01N 2201/12* (2013.01)

(58) Field of Classification Search
CPC ............... C08F 110/06; C08F 2500/20; C08F 2500/12; C08F 2500/15
USPC ............................................ 702/25, 182–185
See application file for complete search history.

(56) References Cited

U.S. PATENT DOCUMENTS 7,173,239 B2 * 2/2007 DiFoggio .................. 250/269.1
8,714,246 B2 * 5/2014 Pop et al. ..................... 166/264

* cited by examiner

*Primary Examiner* — Edward Raymond
(74) *Attorney, Agent, or Firm* — Abelman, Frayne & Schwab

(57) ABSTRACT

A system and a method for calculating the cetane number, pour point, cloud point and aniline point of a gas oil fraction of crude oil from the density and ultraviolet visible spectroscopy of a sample of the crude oil.

24 Claims, 3 Drawing Sheets

CHARACTERIZATION OF CRUDE OIL BY ULTRAVIOLET VISIBLE SPECTROSCOPY

RELATED APPLICATION

This application claims the benefit of U.S. Provisional Patent Application No. 61/445,208 filed Feb. 22, 2011, the disclosure of which is hereby incorporated by reference.

FIELD OF THE INVENTION

This invention relates to a method and process for the evaluation of samples of crude oil and its fractions by ultraviolet visible spectroscopy, avoiding the need to conduct crude oil assays.

BACKGROUND OF THE INVENTION

Crude oil originates from the decomposition and transformation of aquatic, mainly marine, living organisms and/or land plants that became buried under successive layers of mud and silt some 15-500 million years ago. They are essentially very complex mixtures of many thousands of different hydrocarbons. Depending on the source, the oil predominantly contains various proportions of straight and branched-chain paraffins, cycloparaffins, and naphthenic, aromatic, and polynuclear aromatic hydrocarbons. These hydrocarbons can be gaseous, liquid, or solid under normal conditions of temperature and pressure, depending on the number and arrangement of carbon atoms in the molecules.

Crude oils vary widely in their physical and chemical properties from one geographical region to another and from field to field. Crude oils are usually classified into three groups according to the nature of the hydrocarbons they contain: paraffinic, naphthenic, asphaltic, and their mixtures. The differences are due to the different proportions of the various molecular types and sizes. One crude oil can contain mostly paraffins, another mostly naphthenes. Whether paraffinic or naphthenic, one can contain a large quantity of lighter hydrocarbons and be mobile or contain dissolved gases; another can consist mainly of heavier hydrocarbons and be highly viscous, with little or no dissolved gas. Crude oils can also include heteroatoms containing sulfur, nitrogen, nickel, vanadium and other elements in quantities that impact the refinery processing of the crude oil fractions. Light crude oils or condensates can contain sulfur in concentrations as low as 0.01 W %; in contrast, heavy crude oils can contain as much as 5-6 W %. Similarly, the nitrogen content of crude oils can range from 0.001-1.0 W %.

The nature of the crude oil governs, to a certain extent, the nature of the products that can be manufactured from it and their suitability for special applications. A naphthenic crude oil will be more suitable for the production of asphaltic bitumen, a paraffinic crude oil for wax. A naphthenic crude oil, and even more so an aromatic one, will yield lubricating oils with viscosities that are sensitive to temperature. However, with modern refining methods there is greater flexibility in the use of various crude oils to produce many desired type of products.

A crude oil assay is a traditional method of determining the nature of crude oils for benchmarking purposes. Crude oils are subjected to true boiling point (TBP) distillations and fractionations to provide different boiling point fractions. The crude oil distillations are carried out using the American Standard Testing Association (ASTM) Method D 2892. The common fractions and their nominal boiling points are given in Table 1.

TABLE 1

| Fraction | Boiling Point, ° C. |
|---|---|
| Methane | −161.5 |
| Ethane | −88.6 |
| Propane | −42.1 |
| Butanes | −6.0 |
| Light Naphtha | 36-90 |
| Mid Naphtha | 90-160 |
| Heavy Naphtha | 160-205 |
| Light gas Oil | 205-260 |
| Mid Gas Oil | 260-315 |
| Heavy gas Oil | 315-370 |
| Light Vacuum Gas Oil | 370-430 |
| Mid Vacuum Gas Oil | 430-480 |
| Heavy vacuum gas oil | 480-565 |
| Vacuum Residue | 565+ |

The yields, composition, physical and indicative properties of these crude oil fractions, where applicable, are then determined during the crude assay work-up calculations. Typical compositional and property information obtained from a crude oil assay is given in Table 2.

TABLE 2

| Property | Unit | Property Type | Fraction |
|---|---|---|---|
| Yield Weight and Volume % | W% | Yield | All |
| API Gravity | ° | Physical | All |
| Viscosity Kinematic @ 38° C. | ° | Physical | Fraction boiling >250° C. |
| Refractive Index @ 20° C. | Unitless | Physical | Fraction boiling <400° C. |
| Sulfur | W% | Composition | All |
| Mercaptan Sulfur, W% | W% | Composition | Fraction boiling <250° C. |
| Nickel | ppmw | Composition | Fraction boiling >400° C. |
| Nitrogen | ppmw | Composition | All |
| Flash Point, COC | ° C. | Indicative | All |
| Cloud Point | ° C. | Indicative | Fraction boiling >250° C. |
| Pour Point, (Upper) | ° C. | Indicative | Fraction boiling >250° C. |
| Freezing Point | ° C. | Indicative | Fraction boiling >250° C. |
| Microcarbon Residue | W% | Indicative | Fraction boiling >300° C. |
| Smoke Point, mm | mm | Indicative | Fraction boiling between 150-250 |
| Octane Number | Unitless | Indicative | Fraction boiling <250° C. |
| Cetane Index | Unitless | Indicative | Fraction boiling between 150-400 |
| Aniline Point | ° C. | Indicative | Fraction boiling <520° C. |

Due to the number of distillation cuts and the number of analyses involved, the crude oil assay work-up is both costly and time consuming.

In a typical refinery, crude oil is first fractionated in the atmospheric distillation column to separate sour gas and light hydrocarbons, including methane, ethane, propane, butanes and hydrogen sulfide, naphtha (36°-180° C.), kerosene (180°-240° C.), gas oil (240°-370° C.) and atmospheric residue (>370° C.). The atmospheric residue from the atmospheric distillation column is either used as fuel oil or sent to a vacuum distillation unit, depending on the configuration of the refinery. The principal products obtained from vacuum distillation are vacuum gas oil, comprising hydrocarbons boiling in the range 370°-520° C., and vacuum residue, comprising hydrocarbons boiling above 520° C. The crude assay data help refiners to understand the general composition of the crude oil fractions and properties so that the fractions can be processed most efficiently and effectively in an appropriate refining unit. Indicative properties are used to determine the engine/fuel performance or usability or flow characteristic or composition. A summary of the indicative properties and their determination methods with description are given below.

The cetane number of diesel fuel oil, determined by the ASTM D613 method, provides a measure of the ignition quality of diesel fuel; as determined in a standard single cylinder test engine; which measures ignition delay compared to primary reference fuels. The higher the cetane number; the easier the high-speed; direct-injection engine will start; and the less white smoking and diesel knock after start-up are. The cetane number of a diesel fuel oil is determined by comparing its combustion characteristics in a test engine with those for blends of reference fuels of known cetane number under standard operating conditions. This is accomplished using the bracketing hand wheel procedure which varies the compression ratio (hand wheel reading) for the sample and each of the two bracketing reference fuels to obtain a specific ignition delay, thus permitting interpolation of cetane number in terms of hand wheel reading.

The octane number, determined by the ASTM D2699 or D2700 methods, is a measure of a fuel's ability to prevent detonation in a spark ignition engine. Measured in a standard single-cylinder; variable-compression-ratio engine by comparison with primary reference fuels. Under mild conditions, the engine measures research octane number (RON), while under severe conditions, the engine measures motor octane number (MON). Where the law requires posting of octane numbers on dispensing pumps, the antiknock index (AM) is used. This is the arithmetic average of RON and MON, (R+M)/2. It approximates the road octane number, which is a measure of how an average car responds to the fuel.

The cloud point, determined by the ASTM D2500 method, is the temperature at which a cloud of wax crystals appears when a lubricant or distillate fuel is cooled under standard conditions. Cloud point indicates the tendency of the material to plug filters or small orifices under cold weather conditions. The specimen is cooled at a specified rate and examined periodically. The temperature at which cloud is first observed at the bottom of the test jar is recorded as the cloud point. This test method covers only petroleum products and biodiesel fuels that are transparent in 40 mm thick layers, and with a cloud point below 49° C.

The pour point of petroleum products, determined by the ASTM D97 method, is an indicator of the ability of oil or distillate fuel to flow at cold operating temperatures. It is the lowest temperature at which the fluid will flow when cooled under prescribed conditions. After preliminary heating, the sample is cooled at a specified rate and examined at intervals of 3° C. for flow characteristics. The lowest temperature at which movement of the specimen is observed is recorded as the pour point.

The aniline point, determined by the ASTM D611 method, is the lowest temperature at which equal volumes of aniline and hydrocarbon fuel or lubricant base stock are completely miscible. A measure of the aromatic content of a hydrocarbon blend is used to predict the solvency of a base stock or the cetane number of a distillate fuel Specified volumes of aniline and sample, or aniline and sample plus n-heptane, are placed in a tube and mixed mechanically. The mixture is heated at a controlled rate until the two phases become miscible. The mixture is then cooled at a controlled rate and the temperature at which two phases separate is recorded as the aniline point or mixed aniline point.

To determine these properties of gas oil or naphtha fractions conventionally, these fractions have to be distilled off from the crude oil and then measured/determined using various analytical methods that are laborious, costly and time consuming.

In the field of organic chemistry, UV-visible spectrophotometry, which deals with electronic transitions within molecules, has traditionally provided unique information about aromatic and heteroaromatic compounds which absorb strongly in the UV region (200 nm-400 nm). Despite this and owing to the complex molecular nature of crude oil, UV-visible spectra of these oils are often described as featureless, poorly defined spectra. Specific individual aromatic compounds and components are known to have maxima at well-defined wavelengths.

If the wavelength maxima of known aromatic compounds and components are evaluated and extracted from the UV spectra of crude oils they can be used to formulate indices for the aromatic content of the crude oil. These indices can be related to other properties of the oil, e.g., API gravity, sulfur content, and other selected characteristics that define the quality and nature of the constituent products. Importantly, this information can be obtained relatively rapidly and inexpensively from a UV-visible scan as compared to the prior art assay methods described above.

Any new rapid, direct method to help better understand the crude oil composition and properties from the analysis of whole crude oil will save producers, marketers, refiners and/or other crude oil users substantial expense, effort and time. Therefore, a need exists for an improved system and method for determining the properties of crude oil fractions from different sources and classifying the crude oil fractions based on their boiling point characteristics and/or properties.

SUMMARY OF THE INVENTION

The above objects and further advantages are provided by the present invention which broadly comprehends a system and a method for determining the indicative properties of a hydrocarbon sample. In accordance with the invention, indicative properties (i.e., cetane number, pour point, cloud point and aniline point) of gas oil fraction in crude oils are predicted by density and ultraviolet visible spectroscopy measurement of crude oils. The correlations also provide information about the gas oil properties without fractionation/distillation (crude oil assays) and will help producers, refiners, and marketers to benchmark the oil quality and, as a result, valuate the oils without performing the customary extensive and time-consuming crude oil assays.

BRIEF DESCRIPTION OF THE DRAWINGS

Further advantages and features of the present invention will become apparent from the following detailed description of the invention when considered with reference to the accompanying drawings, in which.

DETAILED DESCRIPTION OF INVENTION

Figure 1:
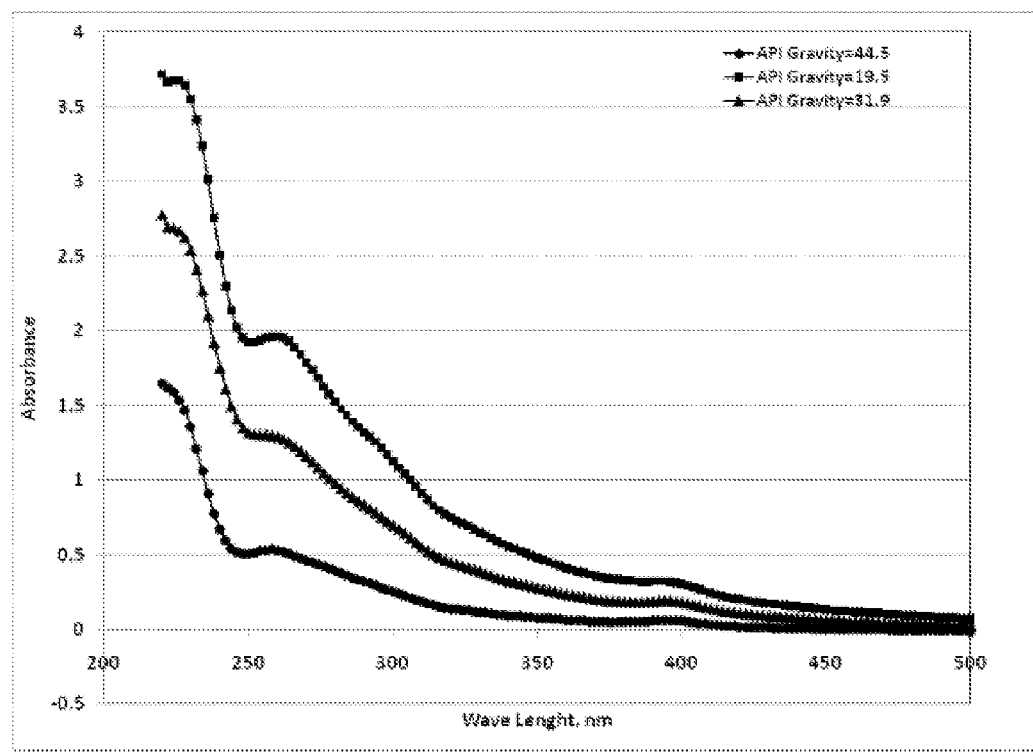
FIG. 1 is a graphic plot of typical ultraviolet visible spectroscopy data for three types of a crude oil sample solution prepared as described below.
Figure 2:
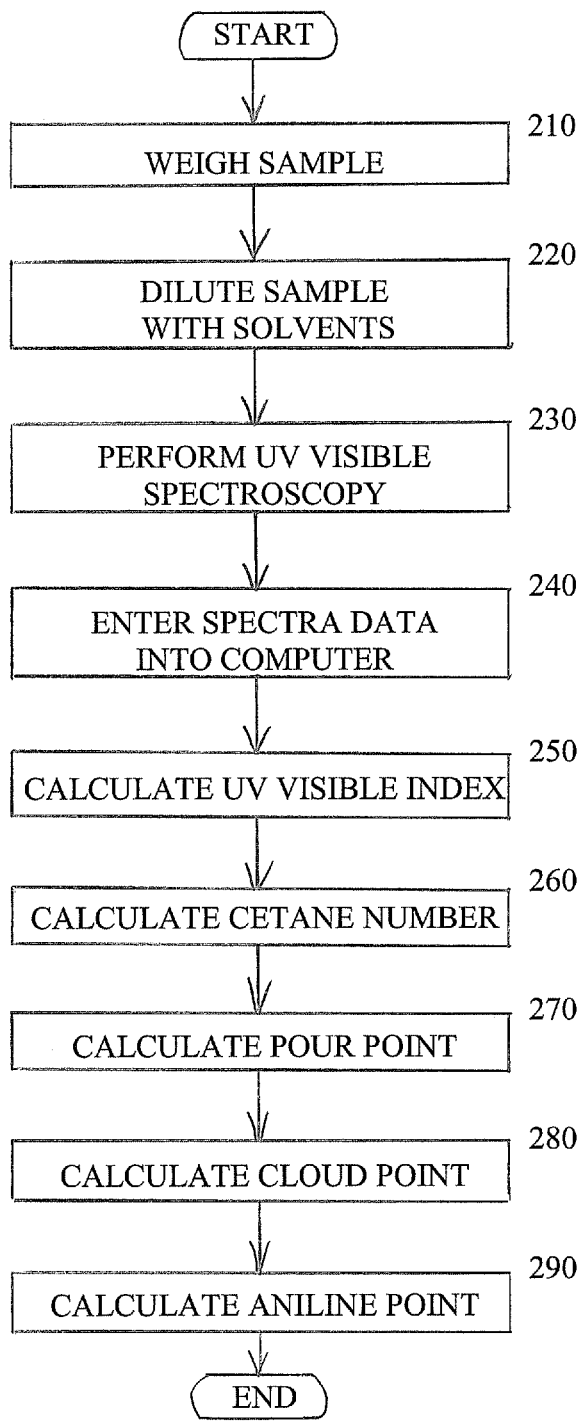
FIG. 2 is a process flow diagram of steps carried out to establish a value for indicative properties of a gas oil fraction, using the system and method of the present invention.

FIG. 2 shows a process flowchart of steps that occur in one embodiment of the invention. Crude oil samples were prepared and analyzed by ultraviolet visible spectrophotometry between 200-500 nm, preferably 220-400 nm, using a Jasco V-530 double beam spectrophotometer. In step 210, a crude oil sample is weighed.

In step 220, solutions were prepared by dissolving a milligram-sized sample of the crude oil in a two-part solvent system consisting of a paraffinic solvent having from 5-20 carbon atoms, preferred solvent being iso-octane, and a polar solvent, preferably, dichloromethane, at a ratio of 90:10% v/v. The polar solvents are selected based on their Hildebrand solubility factors or their two-dimensional solubility parameters. The overall Hildebrand solubility factor is a well known measure of polarity and has been calculated for numerous compounds. See, for example, the Journal of Paint Technology, Vol. 39, No. 505 (February 1967). The solvents can also be described by their two-dimensional solubility parameter. See, for example, I. A. Wiehe, "Polygon Mapping with Two-Dimensional Solubility Parameters", *I&EC Research*, 34, 661-673 (1995). The complexing solubility parameter component, which describes the hydrogen bonding and electron donor-acceptor interactions, measures the interaction energy that requires a specific orientation between an atom of one molecule and a second atom of a different molecule. The field force solubility parameter, which describes the van der Waals and dipole interactions, measures the interaction energy of the liquid that is not destroyed by changes in the orientation of the molecules.

The use of a polar solvent prevents precipitation of asphaltenes from the crude oil sample and ensures that all solutions are translucent for the measurement. The UV absorbance of the crude oil solutions is determined in a conventional one cm quartz cell. The absorbance values of the samples, normalized to 10 mg/L, are summed every even-numbered wavelength between 220 to 400 nm to calculate the characterization index.

In step 230, samples of a variety of crude oil in dilute solution were analyzed by UV-visible spectrophotometry over the wavelengths 220-400 nm. Dilute solutions were prepared by dissolving the oil in a two-part solvent system consisting of iso-octane (90 mL) and dichloromethane (10 mL). In a typical solution preparation, one drop (~6 mg±3 mg) of crude oil from a pre-weighed syringe is added to 100 mL of the solvent solution. The syringe is reweighed to determine the exact amount of the crude oil added. Each crude oil sample is analyzed at two concentration levels, e.g., 60 mg/L and 120 mg/L. Solutions are analyzed in 1 cm quartz cells using a Jasco V-530 double beam spectrophotometer.

The instrument is allowed to warm up for 30 minutes prior to analysis and is auto-zeroed without cells in both sample and reference beams. The reference cell is filled with the solvent mixture then placed in the reference beam. Solutions of the crude oil sample solutions prepared as described above are successively placed in a clean quartz sample cell and the spectra are recorded against the reference solvent blank. The spectra are recorded at a scan speed of 100 nm/min with a fast response time.

Table 3 is an example of a tabulation of values for the sample of Arab heavy crude oil in the wavelength range 220-400 nm, normalized to 10 mg/L concentrations. This data is depicted in the curve of the figure.

TABLE 3

Absorbances of Arab Heavy Crude Oils at Wavelength Ranging from 220-400 nm at 2 nm Interval

| Wave Length | Absor., nm |
|---|---|
| 220 | 3.076 |
| 222 | 2.841 |
| 224 | 2.778 |
| 226 | 2.753 |
| 228 | 2.735 |
| 230 | 2.708 |
| 232 | 2.663 |
| 234 | 2.591 |
| 236 | 2.486 |
| 238 | 2.361 |
| 240 | 2.236 |
| 242 | 2.113 |
| 244 | 1.994 |
| 246 | 1.891 |
| 248 | 1.811 |
| 250 | 1.755 |
| 252 | 1.719 |
| 254 | 1.698 |
| 256 | 1.689 |
| 258 | 1.688 |
| 260 | 1.685 |
| 262 | 1.673 |
| 264 | 1.649 |
| 266 | 1.621 |
| 268 | 1.59 |
| 270 | 1.552 |
| 272 | 1.502 |
| 274 | 1.447 |
| 276 | 1.39 |
| 278 | 1.341 |
| 280 | 1.297 |
| 282 | 1.255 |
| 284 | 1.218 |
| 286 | 1.183 |
| 288 | 1.15 |
| 290 | 1.121 |
| 292 | 1.096 |
| 294 | 1.067 |
| 296 | 1.036 |
| 298 | 1.006 |
| 300 | 0.981 |
| 302 | 0.962 |
| 304 | 0.935 |
| 306 | 0.905 |
| 308 | 0.871 |
| 310 | 0.839 |
| 312 | 0.809 |
| 314 | 0.783 |
| 316 | 0.758 |
| 318 | 0.735 |
| 320 | 0.714 |
| 322 | 0.696 |
| 324 | 0.678 |
| 326 | 0.662 |
| 328 | 0.645 |
| 330 | 0.627 |
| 332 | 0.609 |
| 334 | 0.59 |
| 336 | 0.57 |
| 338 | 0.551 |
| 340 | 0.532 |
| 342 | 0.518 |
| 344 | 0.502 |
| 346 | 0.486 |
| 348 | 0.472 |
| 350 | 0.458 |
| 352 | 0.445 |
| 354 | 0.432 |
| 356 | 0.418 |
| 358 | 0.406 |
| 360 | 0.394 |
| 362 | 0.382 |
| 364 | 0.37 |
| 366 | 0.359 |
| 368 | 0.349 |

TABLE 3-continued

Absorbances of Arab Heavy Crude Oils at Wavelength Ranging from 220-400 nm at 2 nm Interval

| Wave Length | Absor., nm |
|---|---|
| 370 | 0.34 |
| 372 | 0.332 |
| 374 | 0.323 |
| 376 | 0.316 |
| 378 | 0.309 |
| 380 | 0.303 |
| 382 | 0.299 |
| 384 | 0.294 |
| 386 | 0.292 |
| 388 | 0.29 |
| 390 | 0.289 |
| 392 | 0.288 |
| 394 | 0.287 |
| 396 | 0.283 |
| 398 | 0.276 |
| 400 | 0.268 |

Equation (1) shows a crude oil ultraviolet visible index, CUVISI.

$$CUVISI = \sum_{i=220}^{310} (Absorbance_{(2i-220)}/x * 10); \quad (1)$$

where:
Absorbance=absorbance value of the crude oil solution at a specific wavelength over the range 220 nm to 400 nm at 2 nm intervals;
x=the weight of the sample used, in mg.

In step 240, the density and spectra data are entered into a computer. In step 250, the CUVISI is calculated. The data recorded in Table 3 produces a CUVISI of 98.697.

Equations (2) through (5) show, respectively, the cetane number, pour point, cloud point and aniline point of gas oils boiling in the range 180-370° C. that can be predicted from the density and ultraviolet visible spectroscopy index (CUVISI) of crude oils. In step 260, the cetane number is calculated. In step 270, the pour point is calculated. In step 280, the cloud point is calculated. In step 290, the aniline point is calculated. While FIG. 2 shows steps 260 through 290 performed sequentially, they can be performed in any order.

Cetane Number (CET)=$K_{CET}$+$X1_{CET}$*DEN+
$X2_{CET}$*DEN$^2$+$X3_{CET}$*DEN$^3$+$X4_{CET}$*(CUVISI/
100)+$X5_{CET}$*(CUVISI/100)$^2$+$X6_{CET}$*(CUVISI/
100)$^3$+$X7_{CET}$*DEN*(CUVISI/100)  (2);

Pour Point (PP)=$K_{PP}$+$X1_{PP}$*DEN+$X2_{PP}$*DEN$^2$+
$X3_{PP}$*DEN$^3$+$X4_{PP}$*(CUVISI/100)+$X5_{PP}$*
(CUVISI/100)$^2$+$X6_{PP}$*(CUVISI/100)$^3$+
$X7_{PP}$*DEN*(CUVISI/100)  (3);

Cloud Point (CP)=$K_{CP}$+$X1_{CP}$*DEN+$X2_{CP}$*DEN$^2$+
$X3_{CP}$*DEN$^3$+$X4_{CP}$*(CUVISI/100)+$X5_{CP}$*
(CUVISI/100)$^2$+$X6_{CP}$*(CUVISI/100)$^3$+
$X7_{CP}$*DEN*(CUVISI/100)  (4);

Aniline Point (AP)=$K_{AP}$+$X1_{AP}$*DEN+$X2_{AP}$*DEN$^2$+
$X3_{AP}$*DEN$^3$+$X4_{AP}$*(CUVISI/100)+$X5_{AP}$*
(CUVISI/100)$^2$+$X6_{AP}$*(CUVISI/100)$^3$+
$X7_{AP}$*DEN*(CUVISI/100)  (5);

where:
DEN=density of the crude oil sample;
CUVISI=crude oil UV visible index;
and $K_{CET}$, $X1_{CET}$-$X7_{CET}$, $K_{PP}$, $X1_{PP}$-$X7_{PP}$, $K_{AP}$, $X1_{CP}$-$X7_{AP}$, $K_{AP}$, and $X1_{AP}$-$X7_{AP}$ are constants that were developed using linear regression techniques, and which are given in Table 4.

TABLE 4

| Property | Cetane Number (CET) | Pour Point (PP) | Cloud Point (CP) | Aniline Point (AP) |
|---|---|---|---|---|
| K | −472522.2 | −551951.6 | −72809.6 | −168599.5 |
| X1 | 1629297.3 | 1914678.7 | 253698.1 | 553283.7 |
| X2 | 1858806.6 | −2198029.9 | −291533.9 | −598770.2 |
| X3 | 707220.4 | 842964.0 | 112071.8 | 213228.6 |
| X4 | −13648.8 | −15981.5 | −3122.3 | −4138.5 |
| X5 | 17763.9 | 24751.5 | 4976.9 | −562.7 |
| X6 | −7241.0 | −10000.1 | −2006.9 | 239.6 |
| X7 | −656.8 | −4616.8 | −1040.9 | 5250.3 |

The following example is provided. A sample of Arabian medium crude with a density of 0.8828 Kg/l was analyzed by UV-Visible spectroscopy. The spectra data, normalized to 10 mg/L, is shown in Table 5:

TABLE 5

| Wave | Absor., |
|---|---|
| 220 | 2.9442 |
| 222 | 2.8301 |
| 224 | 2.8296 |
| 226 | 2.8382 |
| 228 | 2.8341 |
| 230 | 2.8014 |
| 232 | 2.7397 |
| 234 | 2.6512 |
| 236 | 2.5278 |
| 238 | 2.3901 |
| 240 | 2.2547 |
| 242 | 2.1199 |
| 244 | 1.9885 |
| 246 | 1.8776 |
| 248 | 1.7951 |
| 250 | 1.7386 |
| 252 | 1.7024 |
| 254 | 1.6845 |
| 256 | 1.6781 |
| 258 | 1.6789 |
| 260 | 1.6737 |
| 262 | 1.6580 |
| 264 | 1.6311 |
| 266 | 1.5994 |
| 268 | 1.5665 |
| 270 | 1.5242 |
| 272 | 1.4714 |
| 274 | 1.4128 |
| 276 | 1.3549 |
| 278 | 1.3037 |
| 280 | 1.2559 |
| 282 | 1.2120 |
| 284 | 1.1722 |
| 286 | 1.1353 |
| 288 | 1.1002 |
| 290 | 1.0706 |
| 292 | 1.0416 |
| 294 | 1.0107 |
| 296 | 0.9769 |
| 298 | 0.9436 |
| 300 | 0.9194 |
| 302 | 0.9003 |
| 304 | 0.8711 |
| 306 | 0.8393 |
| 308 | 0.8026 |
| 310 | 0.7688 |
| 312 | 0.7390 |
| 314 | 0.7111 |
| 316 | 0.6869 |
| 318 | 0.6640 |
| 320 | 0.6436 |
| 322 | 0.6252 |
| 324 | 0.6074 |
| 326 | 0.5912 |
| 328 | 0.5746 |
| 330 | 0.5561 |

TABLE 5-continued

| Wave | Absor., |
|---|---|
| 332 | 0.5368 |
| 334 | 0.5175 |
| 336 | 0.4980 |
| 338 | 0.4781 |
| 340 | 0.4590 |
| 342 | 0.4454 |
| 344 | 0.4302 |
| 346 | 0.4162 |
| 348 | 0.4042 |
| 350 | 0.3910 |
| 352 | 0.3786 |
| 354 | 0.3650 |
| 356 | 0.3525 |
| 358 | 0.3407 |
| 360 | 0.3288 |
| 362 | 0.3173 |
| 364 | 0.3069 |
| 366 | 0.2963 |
| 368 | 0.2870 |
| 370 | 0.2787 |
| 372 | 0.2711 |
| 374 | 0.2642 |
| 376 | 0.2574 |
| 378 | 0.2524 |
| 380 | 0.2468 |
| 382 | 0.2425 |
| 384 | 0.2394 |
| 386 | 0.2371 |
| 388 | 0.2359 |
| 390 | 0.2360 |
| 392 | 0.2351 |
| 394 | 0.2342 |
| 396 | 0.2314 |
| 398 | 0.2258 |
| 400 | 0.2174 |

The data recorded in Table 5 for the sample of Arab medium crude oil produces a CUVISI of 94.9748.

Applying equation 2 and the constants from Table 4, $$\text{Cetane Number (CET)} = K_{CET} + X1_{CET}*\text{DEN} + X2_{CET}*\text{DEN}^2 + X3_{CET}*\text{DEN}^3 + X4_{CET}*(\text{CUVISI}/100) + X5_{CET}*(\text{CUVISI}/100)^2 + X6_{CET}*(\text{CUVISI}/100)^3 + X7_{CET}*\text{DEN}*(\text{CUVISI}/100)$$

$$= (-472522.2) + (1629297.3)(0.8828) + (1858806.6)(0.8828)^2 + (-707220.4)(0.8828)^3 + (-13648.8)(94.9748/100) + (17763.9)(94.9748/100)^2 + (-7241.0)(94.9748/100)^3 + (-656.8)(0.8828)(94.9748/100)$$

$$= 59$$

Applying equation 3 and the constants from Table 4, $$\text{Pour Point (PP)} = K_{PP} + X1_{PP}*\text{DEN} + X2_{PP}*\text{DEN}^2 + X3_{PP}*\text{DEN}^3 + X4_{PP}*(\text{CUVISI}/100) + X5_{PP}*(\text{CUVISI}/100)^2 + X6_{PP}*(\text{CUVISI}/100)^3 + X7_{PP}*\text{DEN}*(\text{CUVISI}/100)$$

$$= (-551951.6) + (1914678.7)(0.8828) + (-2198029.9)(0.8828)^2 + (842964.0)(0.8828)^3 + (-15981.5)(94.9748/100) + (24751.5)(94.9748/100)^2 + (-10000.1)(94.9748/100)^3 + (-4616.8)(0.8828)(94.9748/100)$$

$$= -9° \text{C.}$$

Applying equation 4 and the constants from Table 4, $$\text{Cloud Point (CP)} = K_{CP} + X1_{CP}*\text{DEN} + X2_{CP}*\text{DEN}^2 + X3_{CP}*\text{DEN}^3 + X4_{CP}*(\text{CUVISI}/100) + X5_{CP}*(\text{CUVISI}/100)^2 + X6_{CP}*(\text{CUVISI}/100)^3 + X7_{CP}*\text{DEN}*(\text{CUVISI}/100)$$

$$= (-72809.6) + (253698.1)(0.8828) + (-291533.9)(0.8828)^2 + (112071.8)(0.8828)^3 + (-3122.3)(94.9748/100) + (4976.9)(94.9748/100)^2 + (-2006.9)(94.9748/100)^3 + (-1040.9)(0.8828)(94.9748/100)$$

$$= -11° \text{C.}$$

Applying equation 5 and the constants from Table 4, $$\text{Aniline Point (AP)} = K_{AP} + X1_{AP}*\text{DEN} + X2_{AP}*\text{DEN}^2 + X3_{AP}*\text{DEN}^3 + X4_{AP}*(\text{CUVISI}/100) + X5_{AP}*(\text{CUVISI}/100)^2 + X6_{AP}*(\text{CUVISI}/100)^3 + X7_{AP}*\text{DEN}*(\text{CUVISI}/100)$$

$$= (-168599.5) + (553283.7)(0.8828) + (-598770.2)(0.8828)^2 + (213228.6)(0.8828)^3 + (-4138.5)(94.9748/100) + (-562.7)(94.9748/100)^2 + (239.6)(94.9748/100)^3 + (5250.3)(0.8828)(94.9748/100)$$

$$= 66° \text{C.}$$

The method is applicable for naturally occurring hydrocarbons derived from crude oils, bitumens, heavy oils, shale oils and from refinery process units including hydrotreating, hydroprocessing, fluid catalytic cracking, coking, and visbreaking or coal liquefaction.

Figure 3:
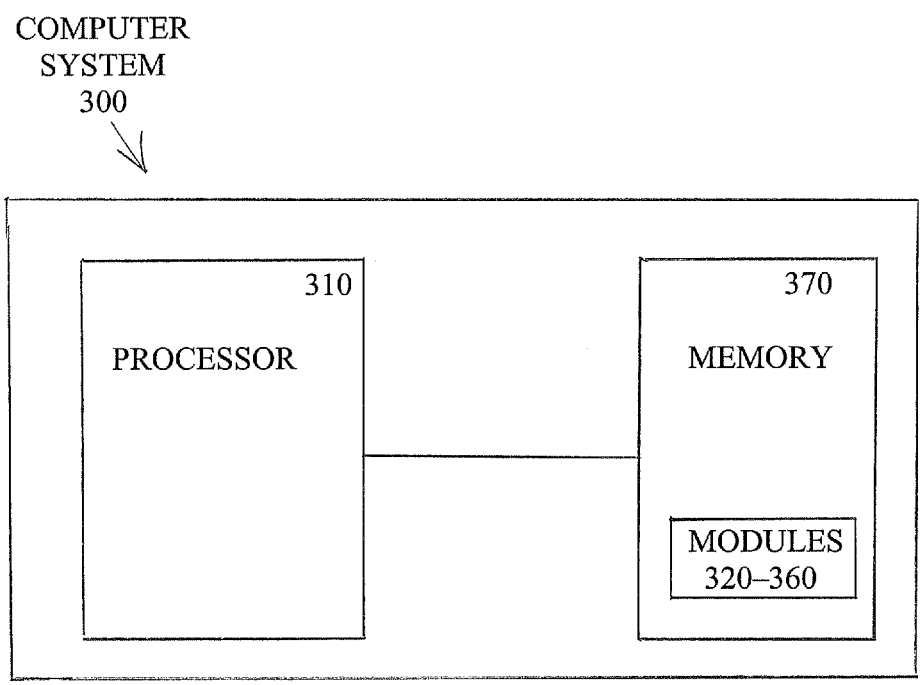
FIG. 3 is a block diagram of components of a system for implementing the invention, according to one preferred embodiment of the present invention.

FIG. 3 illustrates one embodiment of the present invention, implemented in a computer system 300, with a number of modules. Computer system 300 includes a processor 310, and a memory unit 370. Memory unit 370 stores software program modules and associated data, and in particular stores a crude oil UV visible index (CUVISI) calculation module 320, cetane number calculation module 330, a pour point calculation module 340, a cloud point calculation module 350, and an aniline point calculation module 360.

The system and method of the present invention have been described above and with reference to the attached figure; however, modifications will be apparent to those of ordinary skill in the art and the scope of protection for the invention is to be defined by the claims that follow.

We claim:

1. A system for determining indicative properties of a gas oil fraction of a crude oil, based upon ultraviolet visible spectroscopy data derived from a sample of the crude oil and the weight and density of the sample, the system comprising:
    a non-volatile memory device that stores calculation modules and data;
    a processor coupled to the memory;
    a first calculation module that calculates a crude oil ultraviolet visible index value for the gas oil fraction based on the sample's weight and the absorbance values of the spectroscopy data;
    a second calculation module that derives the cetane number for the gas oil fraction of the crude oil as a function of the ultraviolet visible index and density of the sample;
    a third calculation module that derives the pour point for the gas oil fraction of the crude oil as a function of the ultraviolet visible index and density of the sample;
    a fourth calculation module that derives the cloud point for the gas oil fraction of the crude oil as a function of the ultraviolet visible index and density of the sample; and
    a fifth calculation module that derives the aniline point for the gas oil fraction of the crude oil as a function of the ultraviolet visible index and density of the sample.

2. The system of claim 1, wherein the gas oil fraction boils in the nominal range of 180-370° C.

3. A method for operating a computer to determine indicative properties of a gas oil fraction of crude oil boiling in the range of 180-370° C. based upon a sample of the crude oil collected from an oil well, stabilizer, extractor, or distillation tower, the method comprising:

weighing the sample;
preparing said sample for ultraviolet visible spectroscopy analysis by diluting the sample with solvents;
obtaining spectra data for the sample by an ultraviolet visible spectroscopy analysis in a wavelength range from 220-500 nm;
entering into the computer the spectra data for the sample;
calculating an ultraviolet visible index of the gas oil fraction based on the spectra data;
calculating the cetane number for the gas oil fraction as a function of the ultraviolet visible index and density of the sample, and storing the calculated cetane number into a non-volatile memory associated with the computer;
calculating the pour point for the gas oil fraction as a function of the ultraviolet visible index and density of the sample, and storing the calculated pour point into the non-volatile memory associated with the computer;
calculating the cloud point for the gas oil fraction as a function of the ultraviolet visible index and density of the sample, and storing the calculated cloud point into the non-volatile memory associated with the computer; and
calculating the aniline point for the gas oil fraction as a function of the ultraviolet visible index and density of the sample, and storing the calculated aniline point into the non-volatile memory associated with the computer.

4. The method of claim 3, wherein the gas oil fraction boils in the nominal range of 180-370° C.

5. The method of claim 3, wherein the solvent used is a mixture of paraffinic and polar solvents.

6. The method of claim 5, wherein the paraffinic solvent contains from 5-20 carbon atoms.

7. The method of claim 5, wherein the polar solvent is selected based on is Hildebrand solubility factor or by its two-dimensional solubility parameter.

8. The method of claim 7, wherein the polar solvent has a Hildebrand solubility rating of at least 19.

9. The method of claim 7, wherein the two-dimensional solubility factors of the polar solvent are the complexing solubility parameter and the field force solubility parameter.

10. The method of claim 9, wherein the polar solvent's complexing solubility parameter component describes the hydrogen bonding and electron donor acceptor interactions.

11. The method of claim 9, wherein the polar solvent's field force solubility parameter is based on the van der Waals and dipole interactions.

12. The method of claim 5, wherein the paraffinic-to-polar solvent ratio is 70:30 or greater.

13. The method of claim 5, wherein the paraffinic-to-polar solvent ratio is 90:10 or greater.

14. The method of claim 3, wherein the ultraviolet visible spectroscopy data is obtained from an ultraviolet visible spectroscopy analysis in a wavelength range from 220-400 nm.

15. A system for evaluating a crude oil sample and calculating an indicative property, the system comprising:
an ultraviolet visible spectrophotometer;
a non-volatile memory device that stores calculation modules and data, the data including density of the crude oil sample and spectroscopy data obtained from the ultraviolet visible spectrophotometer;
a processor coupled to the non-volatile memory;
a first calculation module that calculates a crude oil ultraviolet visible index value for the gas oil fraction based on the sample's weight and the absorbance values of the spectroscopy data; and
a second calculation module that calculates the indicative property as a function of the ultraviolet visible index and the density of the sample.

16. The system for evaluating a crude oil sample of claim 15, wherein the indicative property being calculated in the second calculation module is the cetane number.

17. The system for evaluating a crude oil sample of claim 15, wherein the indicative property being calculated in the second calculation module is the pour point.

18. The system for evaluating a crude oil sample of claim 15, wherein the indicative property being calculated in the second calculation module is the cloud point.

19. The system for evaluating a crude oil sample of claim 15, wherein the indicative property being calculated in the second calculation module is the aniline point.

20. A method for operating a computer to evaluate a crude oil sample and calculate an indicative property, the method comprising:
weighing the sample;
preparing said sample for ultraviolet visible spectroscopy analysis by diluting the sample with solvents;
obtaining spectra data for the sample by an ultraviolet visible spectroscopy analysis in a wavelength range from 220-500 nm;
entering into the computer the spectra data for the sample;
calculating an ultraviolet visible index of the gas oil fraction based on the spectra data; and
calculating the indicative property as a function of the ultraviolet visible index and density of the sample, and storing the calculated indicative property into a non-volatile memory associated with the computer.

21. The method for operating a computer of claim 20, wherein the indicative property being calculated is the cetane number.

22. The method for operating a computer of claim 20, wherein the indicative property being calculated is the pour point.

23. The method for operating a computer of claim 20, wherein the indicative property being calculated is the cloud point.

24. The method for operating a computer of claim 20, wherein the indicative property being calculated is the aniline point.

* * * * *